(12) United States Patent
Alruhaimi

(10) Patent No.: US 9,622,782 B1
(45) Date of Patent: Apr. 18, 2017

(54) CURVED ALVEOLAR BONE DISTRACTOR

(71) Applicant: KING SAUD UNIVERSITY, Riyadh (SA)

(72) Inventor: Khalid Abdullah Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/295,981

(22) Filed: Oct. 17, 2016

(51) Int. Cl.
| *A61B 17/66* | (2006.01) |
| *A61B 17/88* | (2006.01) |
| *A61C 8/02* | (2006.01) |
| *A61C 8/00* | (2006.01) |

(52) U.S. Cl.
CPC ........ *A61B 17/666* (2013.01); *A61B 17/8866* (2013.01); *A61C 8/0006* (2013.01); *A61C 8/0089* (2013.01)

(58) Field of Classification Search
CPC ............ A61B 17/66; A61B 17/88; A61C 8/00
See application file for complete search history.

(56) References Cited

U.S. PATENT DOCUMENTS

| 5,622,493 A | 4/1997 | Razdolsky et al. |
| 5,807,382 A * | 9/1998 | Chin .................... A61B 17/171 |
| | | 606/105 |
| 6,062,854 A | 5/2000 | Pozzi |
| 6,113,599 A | 9/2000 | Landsberger |
| 6,302,687 B1 * | 10/2001 | King .................... A61B 17/663 |
| | | 433/18 |
| 6,589,250 B2 | 7/2003 | Schendel |
| 2005/0021045 A1 * | 1/2005 | Schendel ............. A61B 17/663 |
| | | 606/105 |
| 2006/0184168 A1 | 8/2006 | Posnick |
| 2007/0162045 A1 * | 7/2007 | Ahmad ................ A61B 17/663 |
| | | 606/105 |

FOREIGN PATENT DOCUMENTS

CN          201267522 Y    7/2009

* cited by examiner

*Primary Examiner* — Christopher Beccia
(74) *Attorney, Agent, or Firm* — Richard C. Litman

(57) ABSTRACT

The curved alveolar bone distractor includes an elongate curved and threaded traction rod supported on opposite ends by anchor brackets. The anchor brackets fix the traction rod onto bony foundation of a patient's jaw. Endcaps cap opposing ends of the traction rod to prevent dislodging and define the extent of working length of the traction rod. A traction bracket freely slides along the traction rod, and the traction bracket is fixed to a movable bony segment. A translator nut is threaded onto the traction rod to abut against a side of the traction bracket. Selective rotation of the translator nut pushes the traction bracket to move the movable bony segment a predetermined distraction distance. When assembled and installed, the working components of the curved distractor are exposed in the oral cavity to the facial side for easy access. Tools are provided to operate the translator nut.

7 Claims, 4 Drawing Sheets

CURVED ALVEOLAR BONE DISTRACTOR

BACKGROUND OF THE INVENTION

1. Field of the Invention

The present invention relates to oral and maxillofacial instruments, and particularly to a curved distractor for oral and maxillofacial reconstruction providing more anatomical conformity for the reconstruction, easy access for regular adjustments, and light weight for comfort and ease of manufacture.

2. Description of the Related Art

One of the most common surgical procedures in alveolar defects repair requires bone augmentation for aesthetic and functional requirements to furnish a foundation to complete dental reconstruction, such as dental implants. Unfortunately, some patients do not have the requisite physiological foundation for the implants. Distraction osteogenesis (DO) is a type of procedure that remedies such deficiencies by inducing additional or new bone and soft tissue growth at the target area. A typical DO procedure augments bone and soft tissues by transecting the target area with the use of a distractor device that maintains a preselected separation between the transected sections. The distractor is incrementally activated over time until the desired separation and induced growth is reached in the distracted area.

Current distractors applied in the anterior alveolar maxillary and mandibular defects are usually constrained to distract the bone in a straight line, tend to be heavy with relatively large components, and/or designed with components submerged under the submucosal layers. These factors may lead to a final reconstruction that does not comply with the correct curvature of the jar arch, patient discomfort, or unforeseen complications. Difficulties in solving problems with distractor bar activation and difficulties in performing adjustments may also arise from the submerged portions of the typical distractor due to limited accessibility. Moreover, the area for reconstruction may not follow a curvilinear line.

Thus, a curved alveolar bone distractor solving the aforementioned problems is desired.

SUMMARY OF THE INVENTION

The curved alveolar bone distractor includes an elongate curved and threaded traction rod supported on opposite ends by anchor brackets. The anchor brackets fix the traction rod onto bony foundation of a patient's jaw. Endcaps cap opposing ends of the traction rod to prevent dislodging and define the extent of working length of the traction rod. A traction bracket freely slides along the traction rod, and the traction bracket is fixed to a movable bony segment. A translator nut is threaded onto the traction rod to abut against a side of the traction bracket. Selective rotation of the translator nut pushes the traction bracket to move the movable bony segment a predetermined distraction distance. When assembled and installed, the working components of the curved distractor are exposed in the oral cavity to the facial side for easy access. Tools are provided to operate the translator nut.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The curved alveolar bone distractor for alveolar reconstruction procedures, generally referred to by reference number 10 in the Figures, provides an ergonomic, curvilinear device that conforms better to the contours of a patient's anterior maxillary and mandibular bone structures. The components of the curved distractor 10 are preferably constructed from lightweight, high-strength, durable materials, such as medical grade metals and plastics, with features that render easy, accessible adjustments to the curved distractor 10.

Figure 1:
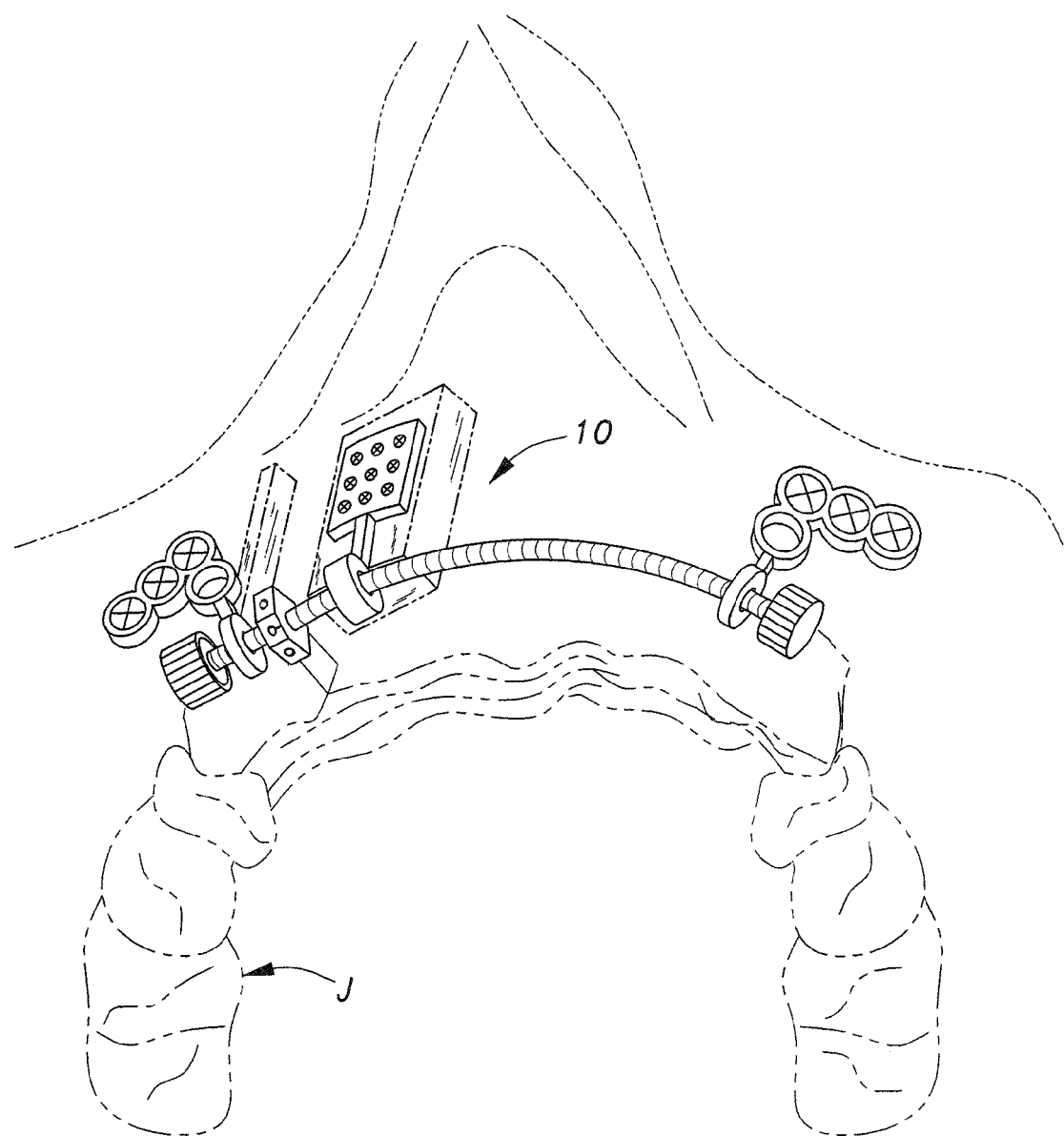
FIG. 1 is an environmental, perspective view of a curved alveolar bone distractor for anterior alveolar reconstruction according to the present invention.
Figure 2:
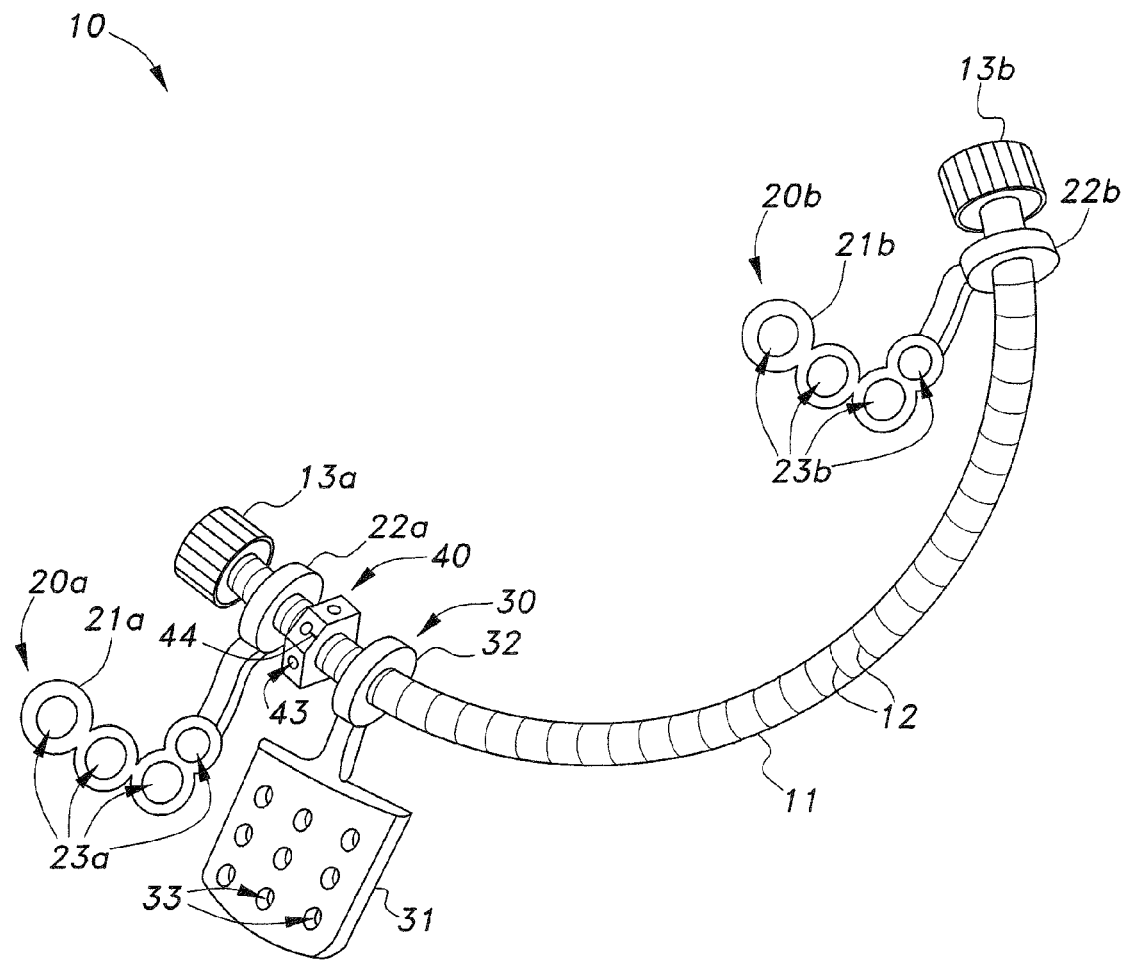
FIG. 2 is a perspective view of the curved distractor of FIG. 1.
Figure 3:
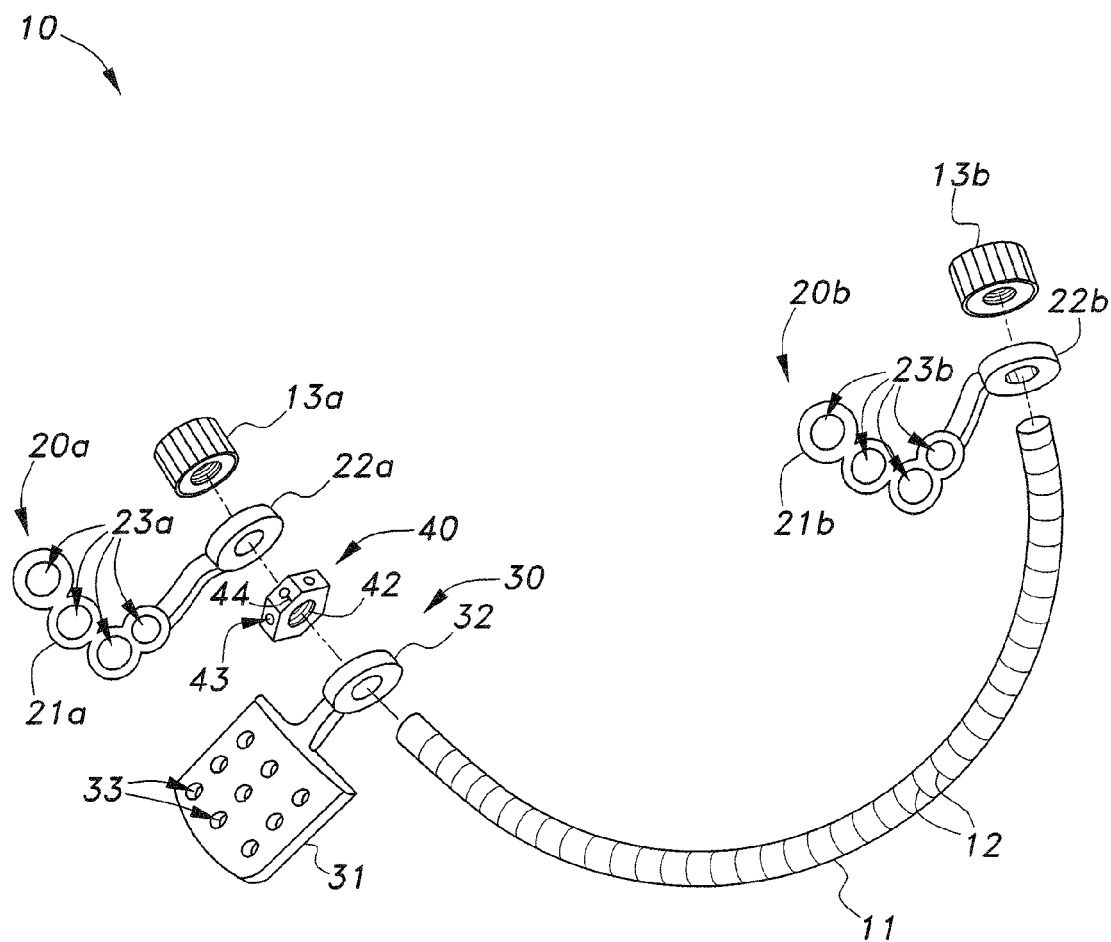
FIG. 3 is an exploded perspective view of the curved distractor of FIG. 1.

As shown in FIGS. 1-3, the curved distractor 10 includes an elongate, curvilinear traction rod 11 configured to follow the natural curved contour of the patient's anterior maxillary and mandibular bone structures. The traction rod 11 is preferably an elongate round bar with threads 12. The traction rod 11 serves as a type of rack for mounting components or enable components to move thereon, especially for distraction. Preferred dimensions of the traction rod 11 include 5 cm of straight length, 2 mm in diameter, and a pitch of about 0.5 mm. It is to be understood that the traction rod 11 is not limited to the above dimensions and may be varied, depending on the application.

A pair of first and second endcaps 13a, 13b cap opposite ends of the traction rod 11. The endcaps 13a, 13b serve as stops defining the limits of any components mounted to or movable on the traction rod 11. Moreover, the endcaps 13a, 13b prevent the traction rod 11 from dislodging once assembled. Each endcap 13a, 13b is preferably a threaded nut that can easily be threaded onto the ends of the traction rod 11. Each endcap 13a, 13b, is about 3 mm in length and 4 mm in diameter. It is to be understood that the endcaps 13a, 13b are not limited to the above dimensions and may be varied depending on the application.

A pair of first and second anchor brackets 20a, 20b slidably mounts to the traction rod 11 near the ends when assembled. The anchor brackets 20a, 20b support the ends of traction rod 11 and fix the traction rod 11 at the desired position along the anterior maxillary and/or mandibular bone structure. Each anchor bracket 20a, 20b is preferably an elongate, generally L-shaped flat plate 21a, 21b with a mounting ring 22a, 22b extending from one end of the plate 21a, 21b and one or more anchor holes 23a, 23b formed thereon. The mounting ring 22a, 22b is not threaded which enables slidable mounting of the respective anchor bracket 20a, 20b onto the traction rod 11 while the anchor holes 23a, 23b facilitate anchoring the opposing ends of the traction rod 11 onto the bone of the patient's mouth. One or more fasteners, such as screws and the like, may be used to fix the anchor brackets 20a, 20b via the anchor holes 23a, 23b. Since the anchor brackets 20a, 20b slide on the traction rod 11 and the portion of the plate 21a, 21b anchoring to the bone must be generally parallel to the contour of the jaw, the mounting ring 22a, 22b is disposed generally perpendicular with respect to the corresponding anchor holes 23a, 23b. The anchor brackets 20a, 20b provides stability to the overall assembled curved distractor 10, and the endcaps 13a, 13b add a further degree of stability by limiting the movements of components mounted to the traction rod 11.

A distractor bracket 30 is also slidably mounted to the traction rod 11 between the anchor brackets 20a, 20b when assembled. The distractor bracket 30 anchors to the desired or preselected moving bony section, i.e., the portion that has been surgically sectioned from the adjacent bony part at one side of the defect and that is to be gradually separated by the curved distractor 10. The distractor bracket 30 is preferably an elongate, generally flat mesh plate 31 with a mounting ring 32 extending from one end of the mesh plate 31 and one or more mounting holes 33 formed on the mesh plate 31. The mesh plate 31 is preferably about 0.5 mm thick. One or more fasteners, such as screws and the like, may be used to fix the distractor bracket 30 via the mounting holes 33. Similar to the previously described anchor brackets 20a, 20b, the mounting ring 32 and the mounting holes 33 are generally oriented perpendicular with respect to each other. The mesh plate 31 is configured to be fixed on the labial surface of the moving bony segment while the mounting ring 32 is exposed to the oral cavity at the level of the traction rod 11. The mounting ring 32 is not threaded so that the distractor bracket 30 is free to move along the traction rod 11.

To move the distractor plate 30 in desired increments, the curved distractor 10 is provided with a translator nut 40 mounted to the traction rod 11 between one of the anchor brackets 20a, 20b and the distractor bracket 30. The translator nut 40 includes internal threads 42 matching the pitch of the threads 12 on the traction rod 11 to securely fix the translator nut 40 thereon. The translator nut 40 may be a hex nut or the like. Preferred dimensions of the translator nut 40 are about 2 mm thick and about 6 mm in diameter. It is to be understood that the translator nut 40 is not limited to the above dimensions and may be varied, depending on the application.

Some concerns with respect to the threaded connection between the translator nut 40 and the traction rod 11 may arise, since the translator nut 40 will follow a curved path defined by the curve of the traction rod 11. However, the relatively small dimensions of these components and the threads thereof minimize much of the potential stripping of the threads. Moreover, the curvature of the traction rod 11 is not drastic to the extent that they may catch and lead to stripping. If the threading becomes an issue, then the threads may be formed with suitable tolerances or angular disposition to compensate.

In use, the translator nut 40 abuts against a side of the mounting ring 32 of the distractor bracket 30. Selective rotation of the translator nut 40 about the traction rod 11 in one direction, e.g., clockwise or counterclockwise, moves or translates the translator nut 40 a predetermined distance along the traction rod 11 as governed by the pitch of the mating threads and number of revolutions of the translator nut 40, e.g., 0.5 mm per each full rotation of the translator nut 40. This pushes the distractor bracket 30 along the translating direction of the translator nut 40; thus, forcing the moving bone section to separate due to the distractor bracket 30 being fixed to the moving bone section. The curved shape of the traction rod 11 ensures that the distraction occurs along a curvilinear path so that the new bone and tissue growth conforms more to the natural contours of the patient's jaw.

Figure 4A:
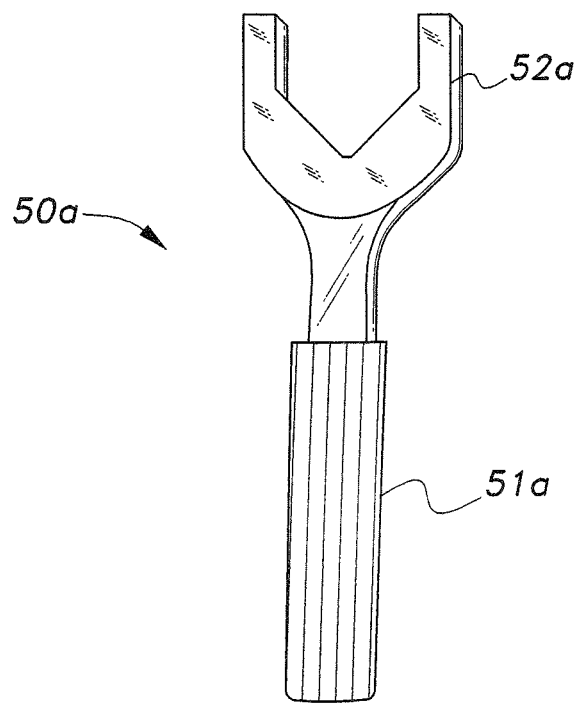
FIG. 4A is a perspective view of a tool for adjusting the curved distractor of FIG. 1.
Figure 4B:
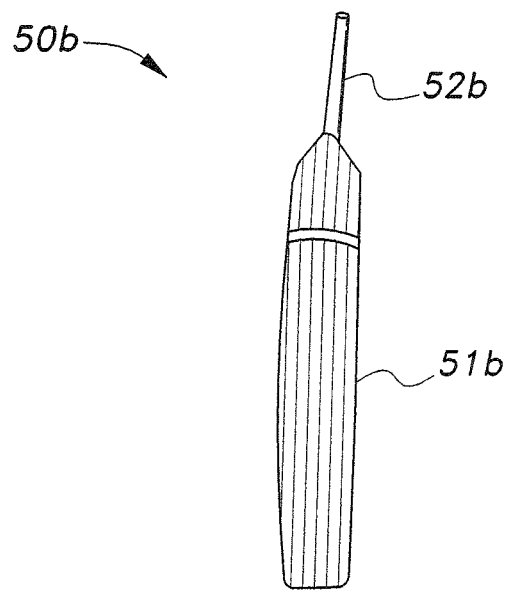
FIG. 4B is a perspective view of another tool for adjusting the curved distractor of FIG. 1.

Operation of the translator nut 40 is facilitated by one or more tools. FIGS. 4A and 4B show examples of tools to enable adjustments of the translator nut 40.

In FIG. 4A, the tool is a manual wrench 50a. The wrench 50a includes an elongate handle 51a and an open-ended jaw 52a extending from one end of the handle 51a. The handle 51a may be provided with grip-enhancing features such as frictional textures or a layer of material with increased friction. The inner profile of the jaw 52a conforms to the sides of the translator nut 40 thereby establishing a suitable grasp on the translator nut 40 for subsequent turning during use.

In FIG. 4B, the tool is a manual pin-lever 50b. The pin-lever 50b includes an elongate handle 51b and an elongate pin 52b extending from one end of the handle 51b. The handle 51b may be provided with grip-enhancing features such as frictional textures or a layer of material with increased friction. The pin 52b may be about 1 mm thick and 1 cm long. One or more sides of the translator nut 40 includes a lever hole 43, and in use, the lever hole 43 receives the pin 52b of the pin-lever 50b for subsequent turning. The lever hole 43 may be about 1 mm in diameter or otherwise dimensioned to receive the thickness of the pin 52b. At least one of the sides of the translator nut 40 may also be provided with indicia, such as a line 44, as a means of gauging the rotated position of the translator nut 40 with respect to the traction rod 11. Either tool may be used during the extended distraction process, however, the manual pin-lever 50b enables finer adjustments due, in part, to its slimmer profile. It is also contemplated that powered versions of the above tools may be used to operate the translator nut 40.

The following is an example of a surgical procedure, assembly of the curved distractor 10, and application of the curved distractor 10 on a defect or target site. Initially, it is noted that one or more of the major components of the curved distractor 10, such as the traction rod 11, the anchor brackets 20a, 20b, and the traction bracket 30, is flexible or bendable to an extent. The oral anatomy of each patient is different from another to varying degrees, and the curved distractor 10 preferably permits necessary adjustment to accommodate the specific anatomy of the patient.

Under local anesthesia, the labial mucoperiosteum of the non-moved alveolar bone at both sides of the defect is surgically exposed together with the labial mucoperiosteum of the bony segment that is preselected to be the free moving part. The planned free moving bony segment is separated from the adjacent non moved bony part by a surgical saw starting labially till it reaches palatally.

The traction bracket 30 is adapted to the labially exposed surface of the free bony segment, e.g. trimming and/or shaping of the mesh plate 31 or shaping of the mounting ring 32 as necessary. The traction bar 11 pass through the mounting ring 32 with the mesh plate 31 in place. The translator nut 40 is threaded to the traction rod 11 from the side of the surgically created bony cut line mesial to the mounting ring 32 and distal to the anchor bracket 20a or 20b, i.e., the translator nut 40 is assembled between the anchor brackets 20a, 20b and adjacent the mounting ring 32.

The ends of the traction rod 11 are inserted through the mounting rings 22a, 22b, respectively, in a passive manner. The anchor plates 21a, 21b are then shaped by, e.g., bending, to conform or adapt to the surfaces of the non-moving bone at both sides of the defect before fixing the anchor plates 21a, 22b and the mesh plate 31. The traction rod 11 is supported by the mounting rings 22a, 22b and the mounting ring 32 during adaptation of the anchor plates 21a, 21b and the mesh plate 31. The anchor plates 21a, 21b are then fixed with fasteners F, such as self-drilling screws, in the labial surface of the non-moving parts of the jaw. Then several fasteners F fix the mesh plate 31 to the labial surface of the moving bony segment.

After fixing the anchor plates 21a, 21b and the mesh plate 31, the free moving bony segment is completely separated from the adjacent non moved bony surfaces at the surgical bony cut line with a small chisel. The endcaps 13a, 13b are tightened to the ends of the traction rod 11 after checking the stability of all components of the curved distractor 10.

The translator nut 40 is rotated with one of the tools, wrench 50a or pin-lever 50b, for about two counter clockwise revolutions, which equates to about 1 mm distance of travel. This process checks the action of the curved distractor 10 and smooth traction of the free bony segment. The soft tissue layers are sutured back and the distraction process is then started by a typically recommended 1 mm rate per day till the targeted distraction distance is reached. When the distraction process is completed and the healing time has been reached, the curved distractor 10 may be easily disassembled and removed with minor surgery.

Thus, it can be seen that the curved distractor 10 provides a relatively simple, convenient, and easy to use device for a distraction process. The curved shape of the traction rod 11 insures that induced growth of new bone and tissue follow a curvilinear path that more closely match the contours of the patient's jaw. The working components of the curved distractor 10, such as the traction rod 11 and the translator nut 40, are exposed to the facial side of the patient's mouth so that they can be easily accessed by the dentist for periodic adjustments of the distraction distance. Moreover, the components of the curved distractor 10 are constructed from relatively lightweight materials which substantially reduce potential discomfort and complications for the patient. The curved distractor 10 may also be provided as a kit with or without the fasteners.

It is to be understood that the present invention is not limited to the embodiments described above, but encompasses any and all embodiments within the scope of the following claims.

I claim:

1. A curved alveolar bone distractor, consisting of:
   an elongate curved traction rod having outer threads thereon along its entire length;
   a pair of anchor brackets slidably mounted adjacent the ends of the traction rod to stably support the traction rod therebetween, each of the anchor brackets having at least one anchor hole to fix the anchor bracket to a bony foundation, each of the anchor brackets being freely slidable on the traction rod, wherein each of the anchor brackets comprises an elongate, substantially L-shaped flat plate having a mounting ring extending from one end of the plate and the at least one anchor hole formed in the plate, the mounting ring coupling each of the anchor brackets to the traction rod and facilitating free sliding movements thereon, the anchor holes being adapted to receive a fastener to fix the anchor bracket to the bony foundation;
   a pair of endcaps capping the ends of the traction rod, the endcaps defining limits for mounting and movement of components on the traction rod;
   a traction bracket slidably mounted to the traction rod, the traction bracket having at least one mounting hole to fix the traction bracket onto a movable bony segment, wherein the traction bracket comprises an elongate, flat mesh plate having a mounting ring extending from one end of the mesh plate, the at least one mounting hole being formed in the mesh plate, the mounting ring coupling the traction bracket to the traction rod and facilitating free sliding movements thereon, the at least one mounting hole being adapted to receive a fastener to fix the traction bracket to the movable bony segment; and
   a rotating translator nut threaded to the traction rod, the translator nut being disposed between one of the anchor brackets and the traction bracket, the translator nut being pushable against a side of the traction bracket to move and separate the movable bony segment;
   wherein selective predetermined rotation of the translator nut in one direction pushes the traction bracket a predetermined distance to define a distraction distance for inducing new bone and tissue growth.

2. The curved alveolar bone distractor according to claim 1, wherein said mounting ring is disposed at an angle different from said at least one anchor hole.

3. The curved alveolar bone distractor according to claim 1, wherein each said endcap comprises a threaded nut.

4. The curved alveolar bone distractor according to claim 1, wherein said mounting ring is disposed at an angle different from the at least one mounting hole.

5. The curved alveolar bone distractor according to claim 1, wherein said translator nut comprises a hex nut having a lever hole formed in at least one side thereof.

6. The curved alveolar bone distractor according to claim 5, further comprising indicia adjacent the lever hole, the indicia providing a visual gauge for determining extent of rotation of said hex nut on said traction rod.

7. A curved alveolar bone distractor kit, consisting of:
   an elongate curved traction rod having outer threads thereon substantially along its entire length;
   a pair of anchor brackets slidably mounted adjacent the ends of the traction rod to stably support the traction rod therebetween, each of the anchor brackets having at least one anchor hole to fix the anchor bracket to a bony foundation, each of the anchor brackets being freely slidable on the traction rod, wherein each of the anchor brackets comprises an elongate, substantially L-shaped flat plate having a mounting ring extending from one end of the plate and the at least one anchor hole formed in the plate, the mounting ring coupling each of the anchor brackets to the traction rod and facilitating free sliding movements thereon, the anchor holes being adapted to receive a fastener to fix the anchor bracket to the bony foundation;
   a pair of endcaps capping the ends of the traction rod, the endcaps defining limits for mounting and movement of components on the traction rod;
   a traction bracket slidably mounted to the traction rod, the traction bracket having at least one mounting hole to fix the traction bracket onto a movable bony segment, wherein the traction bracket comprises an elongate, flat mesh plate having a mounting ring extending from one end of the mesh plate, the at least one mounting hole being formed in the mesh plate, the mounting ring coupling the traction bracket to the traction rod and facilitating free sliding movements thereon, the at least one mounting hole being adapted to receive a fastener to fix the traction bracket to the movable bony segment; and
   a rotating translator nut threaded to the traction rod, the translator nut being disposed between one of the anchor brackets and the traction bracket, the translator nut being pushable against a side of the traction bracket to move and separate the movable bony segment; and tools for rotating the translator nut, wherein the tools include a wrench and a pin-lever, wherein selective predetermined rotation of the translator nut in one direction pushes the traction bracket a predetermined distance to define a distraction distance for inducing new bone and tissue growth.

\* \* \* \* \*